(12) United States Patent
Smith et al.

(10) Patent No.: US 11,751,934 B2
(45) Date of Patent: Sep. 12, 2023

(54) SURGICAL INSTRUMENT AND SYSTEM

(71) Applicant: MEDTRONIC ADVANCED ENERGY, LLC, Minneapolis, MN (US)

(72) Inventors: Jesse Smith, Minneapolis, MN (US); David Hubelbank, Minneapolis, MN (US); John Gearheart, Minneapolis, MN (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 806 days.

(21) Appl. No.: 16/053,917

(22) Filed: Aug. 3, 2018

(65) Prior Publication Data

US 2019/0059982 A1 Feb. 28, 2019

Related U.S. Application Data

(60) Provisional application No. 62/549,560, filed on Aug. 24, 2017.

(51) Int. Cl.
*A61B 18/14* (2006.01)
*A61B 18/12* (2006.01)
(Continued)

(52) U.S. Cl.
CPC .............. *A61B 18/14* (2013.01); *A61B 17/02* (2013.01); *A61B 18/1206* (2013.01);
(Continued)

(58) Field of Classification Search
CPC . A61B 18/14; A61B 18/1206; A61B 18/1233; A61B 18/1402; A61B 18/1442; A61B 18/1445; A61B 18/16; A61B 2018/124; A61B 2018/1253; A61B 2018/126; A61B 2018/1412; A61B 2018/1422; A61B 2018/1452; A61B 2018/1455; A61B 2018/1467; A61B 2018/162; A61B 2018/167; A61B 2018/00875; A61B 2018/1475; A61B 2018/1495; A61B 2018/165;
(Continued)

(56) References Cited

U.S. PATENT DOCUMENTS

2006/0167450 A1* 7/2006 Johnson ............. A61B 18/1445
606/48
2006/0217700 A1* 9/2006 Garito .................... A61B 18/12
606/34

(Continued)

*Primary Examiner* — Thomas A Giuliani
(74) *Attorney, Agent, or Firm* — Patterson Thuente IP

(57) ABSTRACT

An electrosurgical system includes an electrosurgical unit electrically coupled to a surgical retractor. The electrosurgical unit includes an RF output and an RF return. The surgical retractor includes a return pad electrically coupled to the RF return of the electrosurgical unit. The electrosurgical unit includes an RF output configured to be coupled to an electrosurgical device, such as an electrosurgical device configured in a monopolar mode. A controller is configured to determine an impedance in tissue at a surgical area electrically disposed between the RF output and the and the RF return. The surgical retractor includes a handle and a blade configured to interface with tissue. The blade includes a return electrode.

5 Claims, 3 Drawing Sheets

(51) Int. Cl.
  *A61B 17/02* (2006.01)
  *A61B 18/16* (2006.01)
  *A61B 18/00* (2006.01)
  *A61B 17/00* (2006.01)
  *A61B 90/30* (2016.01)

(52) U.S. Cl.
  CPC .......... *A61B 18/16* (2013.01); *A61B 17/0206* (2013.01); *A61B 90/30* (2016.02); *A61B 2017/00026* (2013.01); *A61B 2017/00039* (2013.01); *A61B 2017/00734* (2013.01); *A61B 2017/00907* (2013.01); *A61B 2018/00029* (2013.01); *A61B 2018/00702* (2013.01); *A61B 2018/00726* (2013.01); *A61B 2018/00755* (2013.01); *A61B 2018/00875* (2013.01); *A61B 2018/00892* (2013.01); *A61B 2018/126* (2013.01); *A61B 2018/1253* (2013.01); *A61B 2018/1412* (2013.01); *A61B 2018/1475* (2013.01); *A61B 2018/1495* (2013.01); *A61B 2018/162* (2013.01); *A61B 2018/165* (2013.01); *A61B 2090/309* (2016.02)

(58) Field of Classification Search
  CPC A61B 2018/00702; A61B 2018/00607; A61B 17/02; A61B 17/0206; A61B 17/0293; A61B 2017/00039; A61B 2017/00026
  USPC ........ 606/35, 37, 41, 42, 48, 50–52; 607/98, 607/99, 113, 115, 116
  See application file for complete search history.

(56) References Cited

U.S. PATENT DOCUMENTS

2015/0133911 A1* 5/2015 Batchelor .......... A61B 18/1206
    606/34
2018/0153604 A1* 6/2018 Ayvazyan .......... A61B 18/1477

* cited by examiner

SURGICAL INSTRUMENT AND SYSTEM

CROSS REFERENCE TO RELATED APPLICATION

This Non-Provisional Utility application claims benefit to U.S. Provisional Application No. 62/549,560, filed Aug. 24, 2017, titled "SURGICAL INSTRUMENT AND SYSTEM," the entirety of which incorporated herein by reference.

BACKGROUND

This disclosure relates generally to the field of medical devices, systems and methods for use in surgical procedures. More specifically, this disclosure relates to surgical instruments to manipulate tissue, such as surgical retractors or expanders. In one example, the surgical instruments can be used with electrosurgical devices, units, systems or methods that can provide for cutting, coagulation, hemostasis, or sealing of bodily tissues with an electrosurgical device.

Surgical instruments such as surgical retractors and expanders are used to manipulate tissues including skin, muscles, bone, and organs of a patient and are commonly used in surgery by clinicians. For example, such surgical instruments can separate tissues either at the edges of a surgical incision or wound or can hold back tissues to facilitate the access of tissues under the incision such as to create more room for a clinician to view or to insert other surgical instruments, including electrosurgical devices, into a surgical cavity. Under one distinction, surgical retractors tend to pull the tissue while extractors perform a similar function but tend to push the tissue. For the purposes of this disclosure, such surgical instruments are both generally referred to as surgical retractors.

Working through small incisions, especially in relatively deep surgical pockets, can present many challenges for clinicians such as surgeons. Surgical instruments including electrosurgical devices and surgical retractors are often used in this environment, such as in breast and abdominal surgery. While the surgical instruments, including the electrosurgical devices and surgical retractors are suitable for use in variety of procedures, the examples below may be described with reference to general, plastic, and reconstructive procedures in breast surgery but are not intended to be limited to such procedures.

One example surgical procedure in which electrosurgical devices and surgical retractors are often used includes skin sparing mastectomies and nipple sparing mastectomies. Surgical management of breast cancer has evolved since the radical mastectomy, or Halsted mastectomy. Clinicians have sought procedures to improve oncologic outcomes and combine the techniques of plastic surgery to maximize both cancer treatment and aesthetic effect since the introduction of a skin sparing mastectomy. In a skin sparing mastectomy, all breast tissue and the nipple are removed, but more of the native breast skin is preserved than in a radical mastectomy. The skin sparing mastectomy provides a more enhanced cosmetic result in patients undergoing immediate reconstruction than the radical mastectomy. Although some may consider a skin sparing mastectomy with immediate breast reconstruction the current standard of practice, nipple sparing mastectomy is an advanced surgical option for the treatment of breast cancer is rapidly becoming the preferred surgical option in many patients. The nipple sparing mastectomy provides an effective oncologic surgical outcome and preserves the skin and the nipple-areola complex for improved aesthetics.

Historically, the technique of preserving the nipple-areola complex during mastectomy for breast cancer has been controversial as many felt that this would lead to an unacceptably high rate of breast cancer recurrence. Recent advances in the techniques of preserving the nipple-areola complex during risk-reduction prophylactic mastectomy in a large series of high-risk patients has been described with excellent results in terms of preventing breast cancer. Low local cancer recurrence rates following a nipple sparing mastectomy without irradiation has further supported the adoption of this approach.

As breast surgeons continue to base their interventions on patient safety and oncologic efficacy, the advanced technique of a nipple sparing mastectomy has enabled cosmesis to become a significant goal in breast cancer treatment. Accordingly, patients have increased their interest and demand for nipple sparing mastectomies. For example, genetic testing for breast cancer risk assessment has contributed to the increased the number of nipple sparing mastectomies being performed.

Clinicians seek to improve the techniques used in nipple sparing mastectomies. The type and location of incision used in nipple sparing mastectomy is selected to provide removal of breast tissue, as well as access to the axilla for staging in patients with breast cancer. During the nipple sparing mastectomy, the surgeon has the ability to gain access to tissue from the base of the nipple for assessment of occult cancer. Inframammary incisions and lateral radial incisions are increasingly being utilized during the procedure. Both incisions allow complete removal of the breast tissue, access to the axilla for staging, and ease of obtaining specimens from the base of the nipple. In appropriate patients, the inframammary incision, which is similar to the incision used for breast augmentation, is increasingly becoming the preferred incision location by patients, breast surgeons, and plastic surgeons for improved aesthetic outcomes.

The growing adoption of nipple sparing mastectomy as a surgical option for selected patients has also demonstrated the current surgical limitations of the nipple sparing mastectomy procedure. Some of these limitations include limited incision location options, limited visualization and access through smaller incisions, access to the superior and superior medial aspect of the breast, and the inability or concern in the ability to maintain consistent flap thickness and viability.

SUMMARY

This summary is provided to introduce a selection of concepts in a simplified form that are further described below in the Detailed Description.

The viability of breast flap tissue, for example, can be difficult to detect. This disclosure relates to electrosurgical systems, instruments, and methods to monitor electrical characteristics in tissue at the surgical site, such as during monopolar activation, to monitor conditions in the tissue. For example, rather than rely solely on the electrical characteristics between monopolar device and return pad, this disclosure sets for electrosurgical systems, instruments, and methods of monitoring the signals, such as current, through a monopolar or multi-polar electrosurgical return electrode in a surgical retractor to increase awareness of tissue viability. In one example, an electrosurgical unit can analyze the electrical characteristics received in the surgical retractor at the surgical site to determine changes over time, such as a loss of conductivity of the tissue adjacent to the surgical retractor. For instance, rather than measuring the thermal effects at the site of the electrosurgical device, the systems, instruments, and method provide a return path through the tissue near the surgical retractor and analyze the signal for any loss of conductivity over time.

In one aspect, the disclosure relates to an electrosurgical system having an electrosurgical unit electrically coupled to a surgical retractor. The electrosurgical unit includes an RF output and an RF return. The surgical retractor includes a return pad electrically coupled to the RF return of the electrosurgical unit.

In another aspect, the disclosure relates to an example of an electrosurgical unit. The electrosurgical unit includes an RF output configured to be coupled to an electrosurgical device, such as an electrosurgical device configured in a monopolar mode, and an RF return configured to be coupled to a surgical retractor. The electrosurgical unit also includes a controller operably coupled to the RF output and the RF return. The controller is configured to determine an impedance in tissue at a surgical area electrically disposed between the RF output and the and the RF return.

In still another aspect, the disclosure relates to another example of an electrosurgical unit. The electrosurgical unit includes an RF output configured to be coupled to an electrosurgical device, a first RF return configured to be coupled to one of the electrosurgical device and a return pad dispersive electrode, and a second RF return configured to be coupled to a surgical retractor. The electrosurgical unit includes a controller configured to determine an impedance in tissue at a surgical area electrically disposed between the RF output and the second RF return. The controller is also configured to determine an impedance in tissue at a surgical area electrically disposed between the RF output and the and the first RF return.

In still another aspect, the disclosure relates to a surgical retractor having a handle and a blade configured to interface with tissue. The blade includes a return electrode.

In still another aspect, the disclosure relates to a blade for a surgical retractor, the blade includes an non-conductive base portion having a major surface and a return electrode disposed on the major surface.

DETAILED DESCRIPTION

Figure 1:
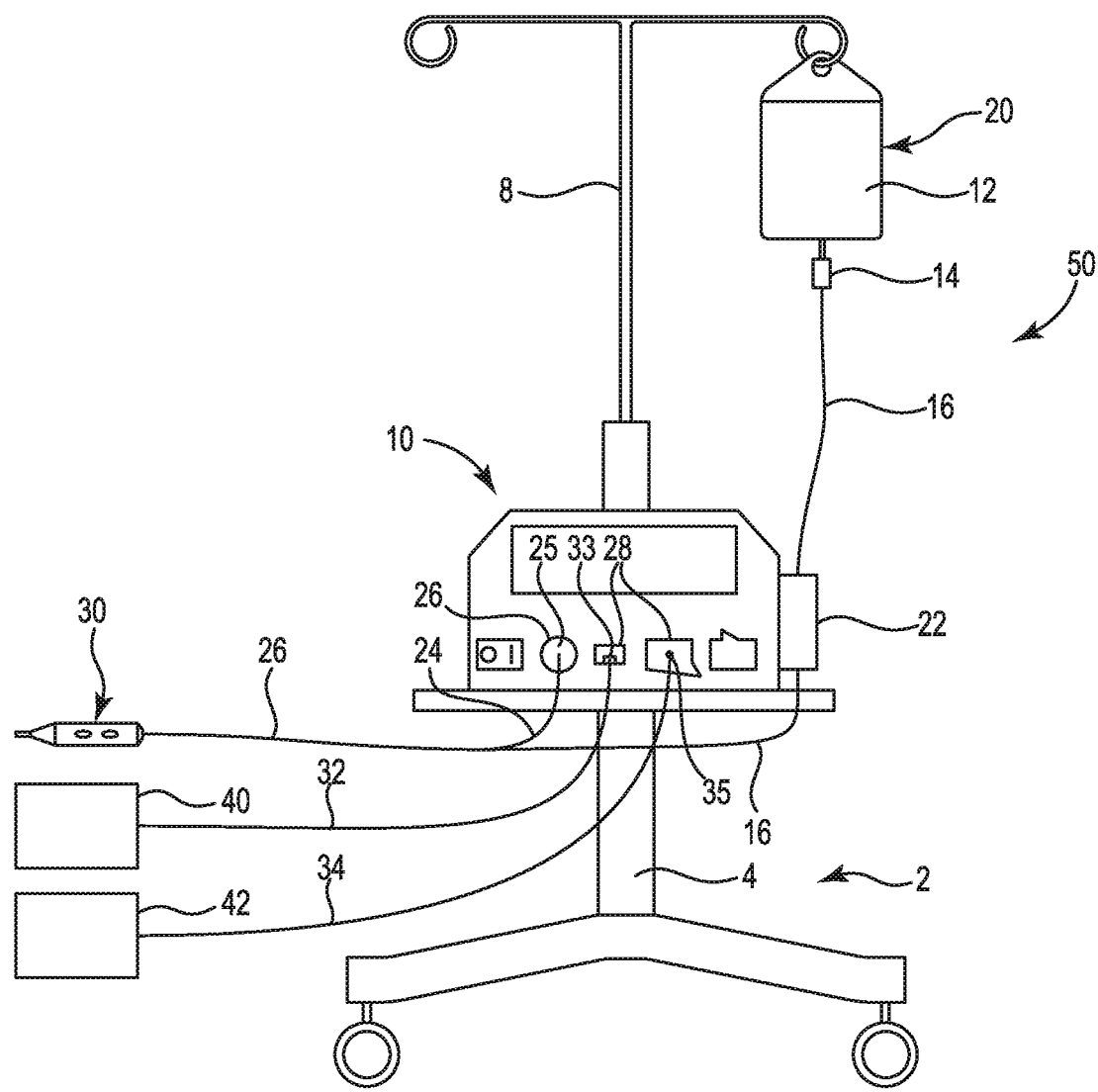
FIG. 1 is a front view illustrating an embodiment of a system according to the present disclosure including an example electrosurgical unit in combination with an example handheld electrosurgical device and an example surgical retractor.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

Electrosurgery includes such techniques as cutting, coagulation, hemostasis, or sealing of tissues with the aid of electrodes energized with a suitable power source. Typical electrosurgical devices apply an electrical potential difference or signal between an active electrode and a return electrode on a patient's grounded body in a monopolar arrangement or between an active electrode and a return electrode on the device in bipolar arrangement to deliver electrical energy to the area where tissue is to be affected. The electrosurgical devices are typically held by a clinician, such as surgeon, and connected to the power source, such as an electrosurgical unit having a power generator, via cabling.

Electrosurgical devices pass electrical energy through tissue between the electrodes to provide coagulation to control bleeding and hemostasis to seal tissue. Electrosurgical devices can also cut tissue through the use of plasma formed on the electrode. Tissue that contacts the plasma experiences a rapid vaporization of cellular fluid to produce a cutting effect. Typically, cutting and coagulation are often performed with electrodes in the monopolar arrangement while hemostasis is performed with electrodes in the bipolar arrangement.

Electrical signals can be applied to the electrodes either as a train of high frequency pulses or as a continuous signal typically in the radiofrequency (RF) range to perform the different techniques. The signals can include a variable set of parameters, such as power or voltage level, waveform parameters such as frequency, pulse duration, duty cycle, and other signal parameters that may be particularly apt or preferred for a given technique. For example, the clinician could cut tissue using a first RF signal having a set of parameters to form plasma and control bleeding using a second RF signal having another set of parameters more preferred for coagulation. The clinician could also use electrodes in a bipolar arrangement or a bipolar electrosurgical device for hemostatic sealing of the tissue that would employ additional RF signals having another set of parameters.

In some examples, two distinct electrosurgical devices, one monopolar and the other bipolar, are used to perform different functions in surgery, such as tissue cutting and coagulating and tissue sealing. For example the clinician could use a monopolar electrosurgical device to cut and coagulate tissue and use a bipolar electrosurgical device to seal the tissue. In another example, some electrosurgical devices are capable of performing multiple techniques such as cutting and coagulating tissue or cutting, coagulating, and sealing tissue, including fluid-assisted sealing of tissue. Several such electrosurgical device are described, for example, in U.S. Pat. No. 8,632,533 to Greeley, et al., U.S. Patent Application Publication No. 2012/000465 to Conley, et al., U.S. Patent Application Publication No. 2011/0178515 to Bloom et al., U.S. Patent Application Publication No. 2016/0045250 to Sylvester, et al., U.S. Patent Application Publication No. 2017/0172646 to Patel, et al., U.S. Patent Application Publication No. 2017/0056099 to Hubelbank, et al., each assigned to the assignee of the present disclosure and incorporated by reference herein in their entireties to the extent they are not inconsistent with the present disclosure.

In some examples, several such multifunction electrosurgical devices that have been developed include a hand piece having two electrodes that are capable of selectively operating in a monopolar mode and a bipolar mode. These devices can be configured as bipolar electrodes connected to a source of bipolar power to operate in a bipolar mode, for example to seal tissue. To operate the same two-electrode device in a monopolar mode, for example to cut tissue, one of the two electrodes may be selectively deactivated and the other of the two electrodes coupled to a source of monopolar power. In this manner, the multifunction device may provide treatment to tissue utilizing one or both electrodes depending upon the desired tissue treatment.

In other examples, a multifunction surgical device can be configured using a plurality of monopolar electrodes that are separately activated and each operated in a monopolar mode. For example, a first monopolar electrode configured as a monopolar blade can be specifically constructed for cutting or desiccating tissue and operated with cutting and coagulating RF energy, which is performed with a relatively high impedance electrode and a high current density to form plasma. A second monopolar electrode can be specifically configured to perform the techniques of hemostatic tissue sealing, which is performed with a relatively lower impedance electrode and a lower current density and a dispersed fluid.

Electrosurgical devices can be operated with electrosurgical units that can include monopolar and bipolar outputs and detect which activation switch on the device is selected. One such electrosurgical unit is available under the trade designation AEx from Medtronic Advanced Energy of Portsmouth, N.H. The electrosurgical unit, in one example, uses a topology of circuit elements, such as a resistor ladder or other circuit configuration, to determine which activation switch of a connected electrosurgical device is selected. In the example, the electrosurgical unit can provide RF signals corresponding with at least three electrosurgical functions such as hemostatic sealing in bipolar configuration, cutting in monopolar configuration, and coagulation in monopolar configuration.

FIG. 1 illustrates a front view of one example of a system 50 that includes an electrosurgical unit 10 in combination with an example handheld electrosurgical device 30 and a surgical retractor 40. The electrosurgical unit 10 provides RF energy to an active electrode on the electrosurgical device 30 to be applied to tissue of a patient and receives a return signal via the surgical retractor 40 in contact with the patient. The electrosurgical unit 10 is able to detect electrical characteristics (impedance, components of impedance such as resistance or reactance, or their changes) of the signal passing through the patient between the electrosurgical device 30 and the surgical retractor 40 to provide information regarding the viability of the tissue adjacent to the surgical retractor 40.

The electrosurgical device 30, in one example, can be a single mode electrosurgical device such as a monopolar device, which may be configured to provide at least one or more of cutting and sealing including electrocautery and coagulation, or a bipolar device, which may be configured to provide hemostatic sealing of tissue in combination with a fluid source 20. In another example, the electrosurgical device 30 can be a multifunction electrosurgical device configurable for use in cutting and sealing including electrocautery and coagulation in a first mode, such as a monopolar mode or a first monopolar mode, and can be configured to provide for hemostatic sealing of tissue in combination with a fluid source 20 in a second mode, such as a bipolar mode or a second monopolar mode, or for other electrical surgical procedures. In still another example, the electrosurgical device 30 can be configured for use in an electrical stimulation mode that may not include cutting, coagulating, or hemostasis.

The surgical retractor 40 can include a conductive return pad configured to interface with tissue on the patient. The return pad on the surgical retractor 40 may be disposed on any surface of the surgical retractor 40 and will provide a return signal from the electrosurgical device 30 to the electrosurgical surgical unit 10. In one example, the surgical retractor 40 may include a blade having a first side configured to interface with the patient, and the return pad is disposed on the first side. The return pad on the surgical retractor 40 is also electrically coupled to the electrosurgical unit 10.

The surgical retractor 40 may be configured in many shapes, sizes, and styles. For example, the general surgical retractor 40 can include a curved, hooked, or angled blade, or paddle, coupled to a handle that, when held in place, can maintain a desired position of tissue. The blade may include a major surface and a smooth edges or a toothed edge to interface with tissue and may be coupled to a light source to illuminate the surgical cavity. The surgical retractor 40 may be part of a kit of several different surgical retractors that are selected to be used in a particular surgery, or a handle may be selectively coupled to one of several blades. The surgical retractor 40 may single use or reusable. The surgical retractor 40 may be handheld, clamped in situ, or connected to robotic arms. In still additional examples, the surgical retractor 40 can be self-retaining and not need to held once inserted by having two or more blades that are mechanically separated, such as via spring, ratchet, worm gear, or other mechanism to pull on multiple sides of a surgical cavity, such as rib spreaders or thoracic retractors. Other configurations of the surgical retractor 40 are contemplated.

The system 50 can be carried on a movable cart 2 having a support member 4 comprising a hollow cylindrical post which includes a platform 6 comprising a pedestal table to provide a flat, stable surface for location of the electrosurgical unit 10. Cart 2 can include a pole 8 having a height that can be adjusted by sliding the pole 8 up and down. Fluid source 20 can be supported at the top of pole 8.

Fluid source 20 may comprise a bag of fluid from which fluid 12 may flow through a drip chamber 14, to delivery tubing 16 and to handheld electrosurgical device 30. In one example, the fluid 12 includes saline and can include physiologic saline such as sodium chloride (NaCl) 0.9% weight/volume solution. Saline is an electrically conductive fluid, and other suitable electrically conductive fluids can be used. In other examples, the fluid may include a nonconductive fluid, such as deionized water, which may still provide advantages over using no fluid and may support cooling of portions of electrosurgical device 30 and tissue or reducing the occurrence of tissue sticking to the electrosurgical device 30.

The fluid delivery tubing 16 in the example passes through pump 22 to convey fluid to the electrosurgical device 30 and control fluid flow. Pump 22 in one example is a peristaltic pump such as a rotary peristaltic pump or a linear peristaltic pump. A peristaltic pump can convey the fluid through the delivery tubing 16 by way of intermittent forces placed on the external surface of the delivery tubing. Peristaltic pumps are often applied during use of the electrosurgical device 30 because the mechanical elements of the pump places forces on the external surface of the delivery tubing and do not come into direct contact with the fluid, which can reduce the likelihood of fluid contamination. Other examples of system 60 might not include a pump, and fluid can be is provided to the electrosurgical device 30 via gravity.

The example electrosurgical unit 10 is configured to provide both monopolar and bipolar RF power outputs to a specified electrosurgical instrument such as electrosurgical device 30. In one example, the electrosurgical unit 10 can be used for delivery of RF energy to instruments indicated for cutting and coagulation of soft tissue and for delivery of RF energy concurrent with fluid to instruments indicated for hemostatic sealing and coagulation of tissue. In one example, the electrosurgical unit 10 is capable of simultaneously powering specified monopolar and bipolar electrosurgical instruments but may include a lock out feature preventing both monopolar and bipolar output from being simultaneously activated.

During monopolar operation of electrosurgical device 30, a first electrosurgical electrode, often referred to as an active electrode, is provided with electrosurgical device 30 while an indifferent, or neutral, electrode is provided in the form of a return pad dispersive electrode 42 located on a patient. For example, the return pad dispersive electrode 42 is typically on the back, buttocks, upper leg, or other suitable anatomical location during surgery. In such a configuration, the return pad dispersive electrode 42 is often referred to as a patient return electrode. An electrical circuit of RF energy is formed between the active electrode and the return pad dispersive electrode 42 through the patient. In some examples, the surgical retractor 40 can be used instead of or in addition to the return pad dispersive electrode 42 to detect electrical characteristics of the tissues adjacent to the surgical retractor 40. An electrical circuit of RF energy is formed between the active electrode and the surgical retractor 40, such as the return pad on the surgical retractor 40, through the tissue between the active electrode and the surgical retractor 40.

During bipolar operation of electrosurgical device 30, a second electrode, often referred to as the return electrode providing a second electrical pole, is provided as part of the device 30. The return pad dispersive electrode 42 is typically not used. An electrical circuit of RF energy is created between the first and second poles of the device 30. The current no longer flows through the patient's body to the ground pad dispersive electrode, but rather through a localized portion of tissue between the poles of the device 30. In some examples, the surgical retractor 40 can be used to provide an additional return path for the electrical signals to detect electrical characteristics of the tissues adjacent to the surgical retractor 40.

The electrosurgical device 30 in the example is connected to electrosurgical unit 10 via cable 24 having plug 25. The electrosurgical unit 10 can include one or more outputs 26 including a monopolar mode output, a bipolar output, or a combination monopolar and bipolar output, which can receive plug 25 and be electrically coupled to the active electrode of the electrosurgical device 30 via cable 24. In some examples, delivery tubing 16 and cable 24 are combined to form a single cable 26. The electrosurgical unit 10 can also include one or more return receptacles 28 that can be electrically coupled to the surgical retractor 40 and also to the return pad dispersive electrode 42. A cable 32 is connected to the surgical retractor 40 and includes plug 33. Plug 33 can be mechanically coupled to the electrosurgical device 10 and electrically connect the return electrode receptacle 28 to the surgical retractor 40. An additional cable 34 is connected to the return pad dispersive electrode 42 and includes plug 35. Plug 35 can be mechanically coupled to the electrosurgical device 10 and electrically connect the return electrode receptacle 28 to the return pad dispersive electrode 42.

In one example, both the surgical retractor 40 and the return pad dispersive electrode 42 are electrically coupled to electrosurgical unit during surgery to detect the impedance of at least the tissue between the active electrode and the surgical retractor 40. In another example, aspects of the surgery may be performed with the surgical retractor 40 disconnected from the electrosurgical unit. In such an example, a surgeon may selectively couple the surgical retractor 40 to the electrosurgical to monitor impedance in the tissue at the surgical site between the active electrode and the surgical retractor 40 in the patient at selected times. A clinician may, in one example, decouple the return pad dispersive electrode 42, or other return conductor, from the electrosurgical unit, and electrically couple the surgical retractor 40 in its place.

The features of electrosurgical unit 10 described are for illustration, and the electrosurgical units suitable for use with electrosurgical device 30 and surgical retractor may include some, all, or other features than those described below. In one example, the electrosurgical unit 10 is capable of operating in at least bipolar mode as well as a bipolar mode and a monopolar mode including multiple functions within the monopolar mode such as a monopolar cutting function, a monopolar coagulation function.

In the monopolar cutting function, monopolar RF energy is provided to the device 30 at a first power level and/or a first waveform (collectively first, or cutting RF energy setting). For example, cutting RF energy for a cut function may be provided at a relatively low voltage and a continuous current (100% on, or 100% duty cycle). Nominal impedance can range between 300 to 1000 ohms for the cutting function. At a power setting of 90 Watts for cutting, voltage can range from approximately 164 to 300 volts root mean square (RMS).

In the monopolar coagulation function, monopolar RF is energy is provided to the electrode at a second power level and/or second waveform (collectively second, or coagulating RF energy setting) that is different than at least one of the first power level or the first waveform. For example, coagulating RF energy for a coagulation function may be provided at a relatively higher voltage than the cut voltage and with bursts of a pulsed current, such as 1% to 6% on and 99% to 94% off, respectively (or 1% to 6% duty cycle). Other duty cycles are contemplated.

The electrosurgical unit 10 may provide bipolar RF energy at a third power level and/or third waveform (collectively third, or hemostatic sealing RF energy setting) along with fluid for a (generally low voltage) hemostasis or tissue sealing function that may be the same as or different than the cutting and coagulating RF settings provided to the device 30 for the cut function or the coagulation function. In one example, hemostatic sealing energy can be provided with a continuous current (100% duty cycle). Nominal impedance can range between 100 to 400 ohms for the hemostatic sealing function. At a power setting of 90 Watts for hemostatic sealing, voltage can range from approximately 95 to 200 volts RMS.

In one example, the electrosurgical unit 10 provides RF energy to the active electrode as a signal having a frequency in the range of 100 KHz to 10 MHz. In some cases, this energy is applied in the form of bursts of pulses. In one example, each burst typically has a duration in the range of 10 microseconds to 1 millisecond. The individual pulses in each burst typically each have a duration of 0.1 to 10 microseconds with an interval between pulses of 0.1 to 10 microseconds. The actual pulses are often sinusoidal and bi-phasic, that is alternating positive and negative amplitudes. Several other features are described in U.S. Pat. No. 8,323,276, to Palanker et al., and incorporated by reference herein in its entirety to the extent it is not inconsistent with the present disclosure.

The electrical surgical unit 10 includes a power switch to turn the unit on and off and an RF power setting display to display the RF power supplied to the electrosurgical device 30. The power setting display can display the RF power setting numerically in a selected unit such as watts.

The example electrosurgical unit 10 includes an RF power selector comprising RF power setting switches that are used to select or adjust the RF power setting. A user can push one power setting switch to increase the RF power setting and push the other power setting switch to decrease the RF power setting. In one example, power setting switches are membrane switches, soft keys, or as part of a touchscreen. In another example, the electrosurgical unit may include more than one power selectors such as a power selector for monopolar power selection and a power selector for bipolar power selection. The electrosurgical unit can also include an RF power activation display having an indicator light that can illuminate when the RF power is activated either via a hand switch on the device 30, a foot switch, or other switch.

The example electrosurgical unit 10 can also include fluid flow rate setting display and flow rate setting selector. The display can include indicator lights, and the flow rate selector can include switches. Pushing one of the flow rate switches selects a fluid flow rate, which is than indicated in display.

While not being bound to a particular theory, the relationship between the variables of fluid flow rate Q (such as in units of cubic centimeters per minute (cc/min)) and RF power setting $P_S$ (such as in units of watts) can be configured to inhibit undesired effects such as tissue desiccation, electrode sticking, smoke production, char formation, and other effects while not providing a fluid flow rate Q at a corresponding RF power setting $P_S$ not so great as to disperse too much electricity and or overly cool the tissue at the electrode/tissue interface. Electrosurgical unit 10 is configured to increase the fluid flow rate Q generally linearly with an increasing RF power setting $P_S$ for each of the three fluid flow rate settings of low, medium, and high.

Electrosurgical unit 10 can be configured to include control of the pump 22. In this example, the speed of the pump 22, and the fluid throughput, can be predetermined based on input variables such as the RF power setting and the fluid flow rate setting. In one example, the pump 22 can be integrated with the electrosurgical unit 10.

Several electrosurgical units, or generators, are described, for example, in U.S. patent application Ser. No. 14/927,999 to Smith, et al., titled RF Output Stage Switching Mechanism, filed Oct. 30, 2015; U.S. patent application Ser. No. 14/928,020 to Hubelbank, et al., titled Finger Switch Circuitry to Reduce Leakage Current, filed Oct. 30, 2015; U.S. patent application Ser. No. 14/927,969 to Smith, et al., titled Power Monitoring Circuitry and Method for Reducing Leakage Current in RF Generators, filed Oct. 30, 2015; and U.S. Patent Application Publication No. 2006/0149225 to McClurken, each assigned to the assignee of the present disclosure and incorporated by reference herein in their entireties to the extent they are not inconsistent with the present disclosure.

While electrosurgical device 30 and surgical retractor 40 are described with reference to electrosurgical unit 10 and other elements of system 50, it should understood the description of the combination is for the purposes of illustrating system 50. It may be possible to use the electrosurgical unit 10 and surgical retractor 40 in other systems including different electrosurgical devices.

Figure 2:
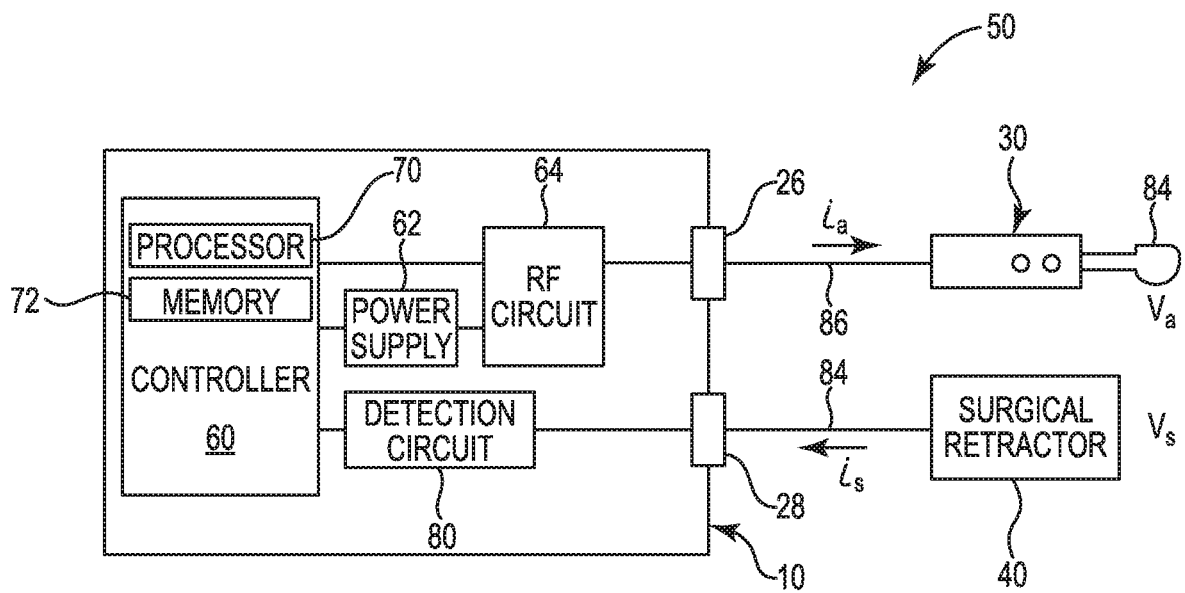
FIG. 2 is a schematic view illustrating the example electrosurgical unit in combination with the example handheld electrosurgical device and the example surgical retractor in the system of FIG. 1.

FIG. 2 illustrates the system 50 including the electrosurgical unit 10 coupled to the electrosurgical device 30 and the surgical retractor 40. The electrosurgical unit 10 includes one or more active electrode output connections 26 that is configured to be electrically coupled to the electrosurgical device 30, such as an electrosurgical device configured in a monopolar mode, and one or more return electrode receptacles 28, one of which is configured to be coupled to the surgical retractor 40. The example electrosurgical unit 10 can include a controller 60, a high voltage power supply 62, and an RF output circuit 64. The power supply 62 provides high voltage power to the RF output circuit 64, which converts high voltage power, for example from a direct current, into RF energy and delivers the RF energy to an active electrode output connection 26. The RF output circuit 64 is configured to generate a plurality of waveforms having various duty cycles, peak voltages, crest factors, and other suitable parameters.

The controller 60 in the example can include a processor 70 operably connected to a memory device 72. Examples of a memory device 72 can include a non-volatile memory device such as a read only memory (ROM), electronically programmable read only memory (EPROM), flash memory, non-volatile random access memory (NRAM) or other memory device, and a volatile memory device such as random access memory (RAM) or other memory device. Memory device 72 can include various combinations of one or both of non-volatile memory devices and volatile memory devices. The microprocessor 70 includes an output port that is operably connected to the power supply 62, the RF output circuit 64, or both that allows the processor 70 to control the output of the electrosurgical unit 10 according to a selected scheme. In some examples, the processor 70 may be substituted with a logic processor or other control circuit.

Any combination of hardware and programming may be used to implement the functionalities of the electrosurgical unit 10. Such combinations of hardware and programming may be implemented in a number of different ways. For example, the programming for the electrosurgical unit 10 may be processor executable instructions stored on at least one non-transitory machine-readable storage medium, such as memory device 72 and the hardware may include at least one processing resource, such as microprocessor 70, to execute those instructions. In some examples, the hardware may also include other electronic circuitry to at least partially implement at least one feature of electrosurgical unit 10. In some examples, the at least one machine-readable storage medium, such as a memory device 72, may store instructions that, when executed by the processor 70, at least partially implement some or all features of electrosurgical unit 10 and. In such examples, electrosurgical unit 10 may include the at least one machine-readable storage medium storing the instructions and the at least one processing resource to execute a method. In other examples, the functionalities of electrosurgical unit 10 and method may be at least partially implemented in the form of electronic circuitry.

The electrosurgical unit 10 also includes a detection circuit 80 electrically coupled to the return receptacle 28 and operably coupled to the controller 60. The features and functions described below as included in the detection circuits such as detection circuit 80, in this disclosure may be, in some examples, included in or performed with the controller 60, vice versa, or some other combination. Furthermore, features and functionality of the detection circuits, such as detection circuit 80, can be implemented from one or more of conductors, circuit elements, hardware, and software.

In the example, the detection circuit 80 is able to detect at least the voltage $V_s$ at the surgical retractor 40, which is provided to the return electrode receptacle 28 and can also be configured to detect the current $i_s$ in the conductor 82 from the surgical retractor 40 to the return electrode receptacle 28. The controller 60 also receives a signal indicating at least one of voltage $V_a$ at the active electrode 84 and the current $i_a$ provided from the output receptacle 26 in conductor 86 to the active electrode 84. The detection circuit 80 and controller 60 operate together to determine the impedance over time in the tissue forming an electrical path between the active electrode 84 and the surgical retractor 40 while treating tissue during surgery. For example, controller 60 can receive a signal representative of the the difference in voltage between the active electrode 84 and the surgical retractor 40 and divide this difference by the measured current from the surgical retractor 40 to calculate the electrical impedance of the tissue in the electrical path between the active electrode 84 and the surgical retractor 40. In some examples, such as if the electrosurgical unit receives a single return signal from the patient, the current provided to the active electrode 84 from the electrosurgical unit 10, $i_a$, is the same, or about the same less some leakage current, as the current from the surgical retractor 40 provided to the electrosurgical unit 10, $i_s$. The calculation of impedance $Z_s$ in the tissue between the active electrode 84 and the surgical retractor 40 at a given time is generally determined by $Z_s = (V_a - V_s)/i_s$.

In one example, controller 60 can include features to present the impedance measurement over time as a visualization to a display or screen. In another example, the controller 60 can include an indicator device to provide an audio indication or visual indication, such as an alarm sound or lights, upon a selected condition of the impedance measurement. The impedance measurement indicative of a selected condition, in one example, can be related to tissue viability of in the surgical area adjacent to the surgical retractor 40. Other selected conditions of interest may be detected via the impedance measurement. A clinician can receive an indication that an impedance threshold representative of the selected condition has been reached, and selectively adjust the RF energy to the active electrode 84, i.e., such as reduce or cut power, or take other action accordingly. Still further, the controller 60 can include a component to automatically adjust power or signals to the active electrode 84 of the electrosurgical device upon detection of a selected condition via the impedance measurement.

Figure 3:
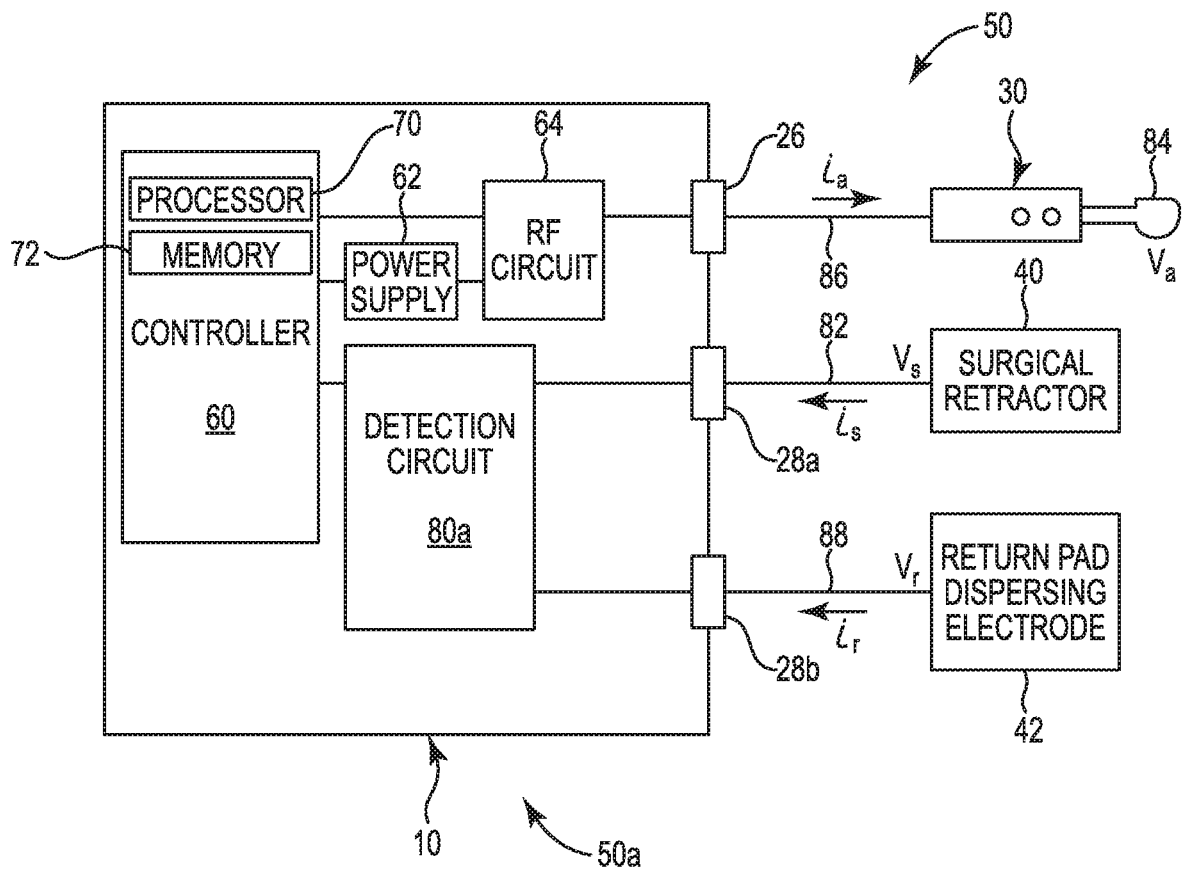
FIG. 3 is a schematic view illustrating another example electrosurgical unit in combination with the example handheld electrosurgical device, an example patient return pad, and the example surgical retractor of FIG. 2.

FIG. 3 illustrates a system 50*a* including an electrosurgical unit 10 coupled to the electrosurgical device 30 and the surgical retractor 40. The electrosurgical unit includes one or more active electrode output connections 26 that is configured to be electrically coupled to the electrosurgical device 30 and a plurality of return electrode receptacles, such as return electrode receptacles 28*a*, 28*b*. The first return electrode receptacle 28*a* is electrically coupled to the surgical retractor 40. The second return electrode receptacle 28*b* is electrically coupled to a return pad dispersive electrode 42, in the example. The second return receptacle 28*b* can also be electrically coupled to a return electrode on a bipolar electrosurgical device. Still further, the electrosurgical unit may include at least three return electrode receptacles, one of which is coupled to the surgical retractor 40, another of which is coupled to the return electrode on a bipolar device, and still another of which is coupled to the a return pad dispersive electrode 42. Other configurations of multiple return receptacles 28 are contemplated.

The example electrosurgical unit 10*a* can also include a controller 60, a high voltage power supply 62, and an RF output circuit 64. The power supply 62 provides high voltage power to the RF output circuit 64, which converts high voltage power, for example from a direct current, into RF energy and delivers the RF energy to an active electrode output connection 26. The RF output circuit 64 is configured to generate a plurality of waveforms having various duty cycles, peak voltages, crest factors, and other suitable parameters. The return receptacles 28*a*, 28*b* are electrically coupled to a detection circuit 80*a*, which is also operably coupled to the controller 60.

In the example, the detection circuit 80*a* is able to detect at least the voltage $V_s$ at the surgical retractor 40, which is provided to the return electrode receptacle 28*a* and can also be configured to detect the current $i_s$ in the conductor 82 from the surgical retractor 40 to the return electrode receptacle 28*a*. The controller 60 also receives a signal indicating at least one of voltage $V_a$ at the active electrode 84 and the current $i_a$ provided from the output receptacle 26 in conductor 86 to the active electrode 84. The detection circuit 80*a* and controller 60 operate together to determine the impedance over time in the tissue forming an electrical path between the active electrode 84 and the surgical retractor 40 while treating tissue during surgery. For example, controller 60 can receive a signal representative of the difference in voltage between the active electrode 84 and the surgical retractor 40 and divide this difference by the measured current from the surgical retractor 40 to calculate the electrical impedance of the tissue in the electrical path between the active electrode 84 and the surgical retractor 40. In some examples, such as if the electrosurgical unit receives multiple return signals from the patient, the current provided to the active electrode 84 from the electrosurgical unit 10, $i_a$, is not the same as the current from the surgical retractor 40 provided to the electrosurgical unit 10, $i_s$. The calculation of impedance $Z_r$ in the tissue between the active electrode 84 and the surgical retractor 40 at a given time is determined by $Z_r = (V_a - V_s)/i_s$.

In some examples, multiple return pads can be included on the surgical retractor 40. Each of these return pads can provide an electrical signal to the electrosurgical unit 10. The electrosurgical unit 10 can analyze each of these signals for relative changes between the signals to determine whether tissue proximate one return pad includes a change in electrical characteristics compared to tissue proximate another return pad. For example, the detection circuit 80*a* is able to detect at least the voltage $V_{s1}, V_{s2}, \ldots V_{sn}$, in each of the return pads n of the surgical retractor 40, which is provided to the return electrode receptacles and can also be configured to detect the current $i_{s1}, i_{s2}, \ldots i_{sn}$, in each of the conductors coupled to the n return pads n of the surgical retractor 40 to the return electrode receptacle 28*a*. The controller 60 also receives a signal indicating at least one of voltage $V_a$ at the active electrode 84 and the current $i_a$ provided from the output receptacle 26 in conductor 86 to the active electrode 84. The detection circuit 80*a* and controller 60 operate together to determine the impedance or impedance over time in the tissue forming an electrical path between the active electrode 84 and the n return pads surgical retractor 40 while treating tissue during surgery and can compare the electrical characteristics to each other to monitor changes or anomalies.

The detection circuit 80a and controller 60 can operate together to determine the impedance or impedance over time in tissue forming an electrical path between the n return pads on the surgical retractor 40, such as two or more return pads on the surgical retractor 40 in the manner similar to a split pad. For example, an electrical signal at an interrogation frequency is provided to return pads on the surgical retractor 40 to measure the impedances in the tissue between the return pads on the surgical retractor 40. In one example, the interrogation frequency can be in the range of 1 kHz to 100 kHz and can be provided even while the electrosurgical device 30 is not activated to monitor impedance in the tissue between the return pads without application of the electrosurgical device 30.

The controller 60 can also receive a signal representative of the difference in voltage between the active electrode 84 and the return pad dispersive electrode 42 and divide this difference by the measured current from the surgical retractor 40 to calculate the electrical impedance of the tissue in the electrical path between the active electrode 84 and the return pad dispersive electrode 42. In the example, the detection circuit 80a is able to detect at least the voltage $V_r$ at the return pad dispersive electrode 42, which is provided to the return electrode receptacle 28b and can also be configured to detect the current $i_r$ in the conductor 88 from the return pad dispersive electrode 42 to the return electrode receptacle 28b. The calculation of impedance in the tissue between the active electrode 84 and the return pad dispersive electrode 42 at a given time is determined by $(V_a-V_r)/i_r$. This impedance measurement can be compared to the impedance measurement in the tissue between the active electrode 84 and the surgical retractor 40 for further insight into the condition of the tissue adjacent to the surgical retractor 40.

The detection circuit 80, 80a in on example may include return electrode monitoring circuitry to monitor contact area between the patient and one or more return pad dispersive electrode 42. The circuitry prevents tissue damage caused by pad burns due to poor pad contact. The return electrode monitoring circuitry forms a resonant system with split electrode pads of the return pad dispersive electrode 42 that are designed to resonate at a specific interrogation frequency. The return electrode monitoring circuitry detects a signal in response to a supplied drive signal at a predetermined clock frequency (e.g., from the controller 60). The return electrode monitoring circuitry produces a voltage indicative of the amplitude (e.g., magnitude) of the waveform indicative of the resonations. As the impedance between the split pads changes, the resonance of the return electrode monitoring circuitry changes as well, which causes the amplitude to change. Thus, by monitoring the changes in the amplitude, the return electrode monitoring circuit determines the magnitude of the impedance between the split pads, which is indicative of adherence of the return pad dispersive electrode 42 to the patient. In one example, surgical retractor 40 can be configured to include split return pads, and the return electrode monitoring circuitry can be applied to detect a selected amount of contact between the tissue at the surgical site and split return pads on the surgical retractor 40.

Figure 4:
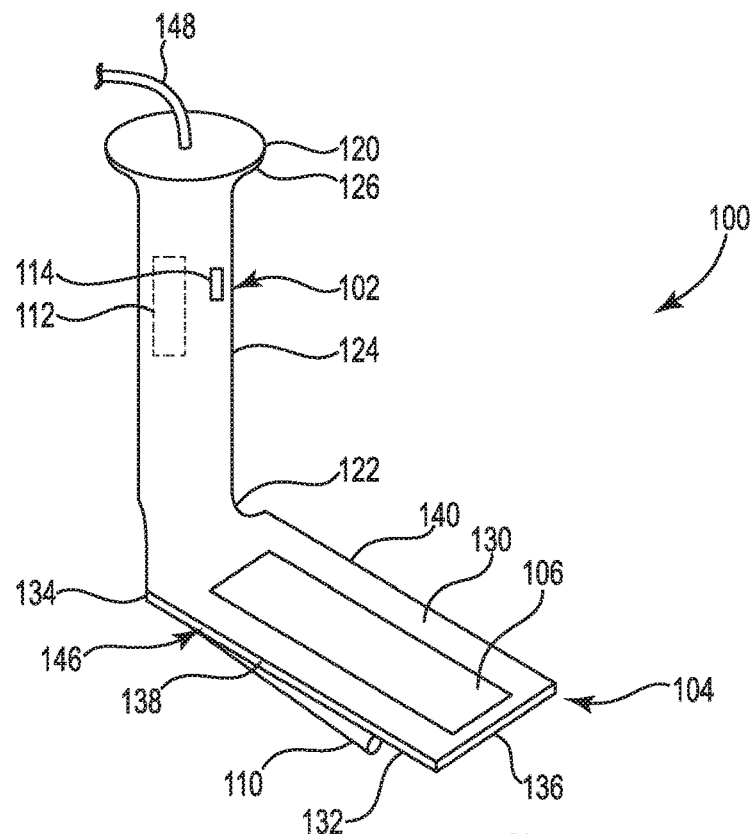
FIG. 4 is a perspective view illustrating an example surgical retractor suitable for use in the system of FIG. 1.

FIG. 4 illustrates a surgical retractor 100 that allows a user to manipulate and tissues of a patient and is an example of surgical retractor 40. The manipulation, for example, may be expansion or retraction of skin, muscle, organs, bone or other tissues. In one example, the surgical retractor 100 may be used to perform surgery on the breast, such as gynecomastia correction, augmentation, mastopexy, reduction, and skin sparing or nipple sparing mastectomies prior to breast reconstruction. The surgical retractor 100 allows for a conservative sized incision for introduction, removal, or replacement of a breast implant. It also facilitates visualization for effective hemostasis in a breast pocket and dissection of the periphery of the breast pocket. Still further, the surgical retractor provides an ability to gauge the viability of breast flap tissue or other tissue at the surgical site using electrosurgical signals that travel through the tissue from the electrosurgical device to the surgical retractor. Additionally, the surgical instrument 100 may be used to perform surgery on a patient's abdomen, pelvis, or trunk and limbs, such as dissection of a pedicled or free flap, like a latissimus dorsi muscle for reconstruction as well as to gauge the viability of such tissue in contact with the surgical retractor 100.

The surgical retractor 100 has a handle 102, a blade 104, and a return electrode 106. In the example, the surgical retractor 100 can also includes a light 110 disposed on the blade 104, a power source 112 (shown in phantom) disposed within the surgical retractor 100, such as the within the handle 102, and a light switch 114 disposed on the handle 102.

The handle 102 and the blade 104 may be made of a rigid, sterilizable, electrically insulative material such as a synthetic polymer. The synthetic polymer can include polycarbonate, acrylonitrile-butadiene-styrene, or other suitable materials. Lightweight materials also permit a clinician to use the device over long periods of time with less fatigue. In one example, the surgical retractor 100 is composed of materials permitting it to be readily and economically disposable.

The handle 102 includes a proximal end 120, a base end 122, and an intermediate portion 124. The handle 102 a can be configured to be hand-held and may have a grip handle, a cylindrical grip, or other ergonomic design to be held by a user. In some examples, the handle 102 has protrusions such as vertical or horizontal ridges, to facilitate comfortable or ergonomic holding by the user. The handle 102 can include a flared top 126 near the proximal end 120 to allow the handle 102 to be more easily gripped and held. The handle 102 may be made of a soft, foam plastic material to provide a comfortable, resilient grip. In some examples, the handle 102 is shaped to permit connection to a clamp, a holding mechanism, or other device to mount the surgical retractor 100 to a surgical table or to a floor stand.

The blade 104 extends from the base end 122 of the handle 102 and may be generally flat and generally rectangular in profile. Other blade profiles or cross-sections sufficient to manipulate the patient's tissues may be used, such as cylindrical, paddle-shaped, rectangular, or conical. In some examples, at least a portion of the length of the blade 104 is generally oblique to the handle 102. In the depicted embodiments, the blade 104 can be generally perpendicular to the handle 102. The blade 104 could also be at any angle to the handle 102. In some examples, the angle of blade 104 may be adjustable with respect to the handle 102, such as by inclusion of a hinge in the blade or at the attachment point of the blade with the handle 102, such as at the base end 122. In some examples, the blade 104 may be detachable from and attachable to the handle 102, such as by inclusion of an attachment mechanism in the blade 104 or the handle 102. For example, a user may detach a first blade of a selected first configuration from the handle and attached a second blade having a selected second configuration to the handle.

Alternatively, a user may detach a first handle of a selected first configuration from the blade and attached a second handle having a selected second configuration to the blade.

The blade 104 includes a first major surface 130, which is configured to interface with tissue during surgery, and an opposite, second major surface 132. The blade 104 can include a base 134 and tip 136. The blade 104 can include first and second side edges 138, 140, and a tip edge 142. The width of the blade 104 can be described as the distance between the first and second side edges 138, 140, and the length of the blade can be described as the distance between the base 134 and the tip 136.

In some examples, the blade 104 includes a flared tip (not shown), where the tip is oblique to the adjacent portion of the blade 104. Such a flared tip can facilitate movement of the tip among the patient's tissues. In some examples, the blade 104 has tines, or teeth (not shown), at the tip 136 to grip or maneuver the tissues. In some examples, the blade is extendable or adjustable (not shown). For example, the length or width of the blade may be made longer or shorter, for example, by sliding one portion of the blade relative to another portion.

The blade 104 includes a base portion 146 formed of the rigid, sterilizable, electrically insulative material such as the synthetic polymer forming the first major surface 130 and the second major surface 132. A return electrode 106 is affixed to the base portion 146 such as on the first major surface 130. The return electrode 1 is formed from electrically conductive material such as metal and may comprise stainless steel, titanium, gold, silver, platinum or any other suitable material. The configuration of the return electrode 106 can vary. For example, the return electrode 106 may be formed as a pad conductor having a rectangular profile or some other geometry, may be a narrow conductor strip extending along the length of the blade 104, may be a grid of narrow conductors in a mesh-like arrangement, or some other suitable configuration. The return electrode 106 may be a single foil configuration or a split foil configuration and may include one or more single foil or split foil return electrodes. In some examples, a return electrode may be attached to the second major surface 134 in addition to or instead of the first major surface 132. In the case of electrodes disposed on both the first and second major surfaces 132, 134, the electrodes may be electrically coupled to each other or electrically isolated from each other on the blade 104.

The return electrode 106 is electrically coupled to one or more electrical conductors that can be disposed on or within the surgical retractor 100 such as within the handle 102. Multiple electrical pathways are electrically coupled to the return electrode 106 in the case of a slit foil configuration, multiple return electrodes, or other configuration. In the case of a multiple conductors such as split foil pad, the current to each of the foils could be differentiated to measure relative conductivity of the tissue above both foils in relation to each other. Electrical pathways within the handle 102 can be formed as conductive arms, wires, traces, other conductive elements, and other electrical pathways formed from electrically conductive material such as metal and may comprise stainless steel, titanium, gold, silver, platinum or any other suitable material. The electrical pathways can extend from the handle 102 via cable 148 at proximal end 120. In one example, cable 148 can include one or more connectors (not shown) that can be electrically and mechanically coupled to the proximal end 120 and to an electrosurgical unit, such as electrosurgical unit 10. Cable 148 can correspond with cable 32 and include one or more conductors, such as conductor 82, as electrical pathways.

The light 110 can be used to illuminate the tissues adjacent to or proximate the blades such as the surgical cavity. The light 110 may located at the base end 122 of the handle 102, on the blade 104, such as on the second major surface 134, or elsewhere on the surgical retractor 100. The light 110 can include one or more light emitting diodes (LEDs) that may be enclosed in a translucent, including transparent, covering. The light 110 may include electrical or thermal insulation.

The power source 112 may be disposed within the handle 102 and may include at least one battery or other energy storage element to provide enough power to last through surgery. A battery life of four to five hours may be sufficient. In some examples, the power source 112 is removable so that it may be recharged.

In addition, the surgical retractor 100 may include a light switch 114 to selectively electrically couple the power source 112 to the light 110. In one example, the light switch may be a push button or toggle switch disposed on the handle 102 near the location of a clinician's thumb or forefinger for easy accessibility. In some examples, the light switch 114 may be used to select one of a plurality of levels of illumination from the light 110. The light switch 114 may include a switch guard formed into the handle 102 to reduce the likelihood that the light 110 is inadvertently activated or deactivated.

The surgical retractor 100 may include additional features or functionalities. For example, the handle 102 or blade 104 may have a channel or tube that can be connected to a suction device, such as a suction tap in an operating room, to provide aspiration of gas or fluid from the surgical region or surgical cavity. Additionally, the surgical retractor can include a camera or be configured to accept a camera. In one example, the camera includes a wireless transmitter that can be located within the handle 102.

Figure 5:
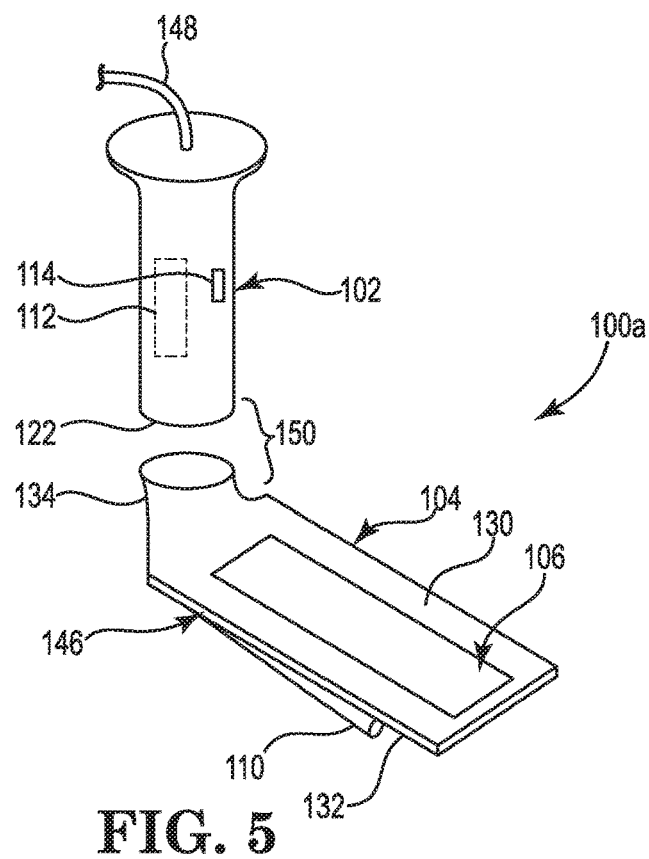
FIG. 5 is a perspective view illustrating another example surgical retractor suitable for use in the system of FIG. 1.

FIG. 5 illustrates another surgical retractor 100a having a blade 104 detachable from the handle 102. The blade 104 includes a return electrode 106 attached to the first major surface 130. The surgical retractor 100a can include features and functionality of surgical retractor 100. For example, the surgical retractor 100a can also include a blade 104 having a light 110 disposed on the second major surface 132. A power source 112 can be disposed within the handle 102, and a light switch 114 disposed on the handle. The surgical retractor 100a further includes a mechanical coupling 150 proximate the base end 122 of the handle 102 and the base 134 of the blade such that the base end 122 of the handle 102 can be selectively coupled to or decoupled from the base of the blade 104. Additionally, the mechanical coupling 150 can include one or more electrical couplings, such as a detachable electrical connection to selectively electrically connect the return electrode 106 to an electrical pathway in the cable 148 in cases when the blade 102 is mechanically coupled to the handle 102. In the case of the surgical retractor 100a including light 110, the mechanical coupling can also include a detachable electrical connection to selectively electrically connect the light 110 to the power source 112 in cases when the blade 102 is mechanically coupled to the handle 102.

Although the present disclosure has been described with reference to preferred embodiments, workers skilled in the art will recognize that changes can be made in form and detail without departing from the spirit and scope of the present disclosure.

What is claimed is:

1. An electrosurgical system, comprising:
an electrosurgical unit having RF output operably coupled to a RF active receptacle including an output conductor and an RF return operably coupled to a plurality of RF return receptacles, the RF output and RF return to provide an RF signal configured to be received in a tissue of a patient;
an electrosurgical device operably coupled to the RF active receptacle and having an active electrode configured to interface with the patient at a surgical site in the tissue;
a surgical retractor having a blade and a handle attached to the blade, the blade configured to push or pull the tissue of the patient at a first location remote from the surgical site, the blade including a major surface, the major surface configured to be oblique to the handle, the surgical retractor having a retractor electrode coupled to the electrosurgical unit to interface with the RF signal in the tissue of the patient, the retractor electrode consisting of a conductive return pad affixed to the major surface;
a return pad dispersive electrode configured to interface with the tissue of the patient at a second location remote from the surgical site, wherein the plurality of RF return receptacles of the electrosurgical unit includes a first RF return receptacle and a second RF return receptacle, wherein the surgical retractor is electrically coupled to the first RF return receiptacle and the return pad dispersive electrode is electrically coupled to the second RF return receptacle;
wherein the electrosurgical unit is configured to determine a first impedance in the tissue between the active electrode of the electrosurgical device and the return pad dispersive electrode and second impedance in the tissue between the active electrode of the electrosurgical device and the retractor electrode of the surgical retractor.

2. The electrosurgical system of claim 1 wherein each determined impedance is a determined change of impedance over time.

3. The electrosurgical system of claim 1 wherein the electrosurgical unit is configured to output each determined impedance.

4. The electrosurgical system of claim 3 wherein the output includes a visualization on a screen or display.

5. The electrosurgical system of claim 1, wherein the electrosurgical unit is configured to compare the first impedance in the tissue between the active electrode of the electrosurgical device and the return pad dispersive electrode to the second impedance in the tissue between the active electrode of the electrosurgical device and the retractor electrode of the surgical retractor.

* * * * *